United States Patent [19]

Hugues et al.

[11] Patent Number: 5,298,248
[45] Date of Patent: Mar. 29, 1994

[54] METHOD FOR CONTINUOUS LIBERATION OF ACTIVE CONSTITUENTS INTO WATER

[75] Inventors: Porte Hugues, Caluire; Torres Ghislaine, Lyons, both of France

[73] Assignee: Rhone-Poulenc Sante, Antony, France

[21] Appl. No.: 835,079

[22] Filed: Feb. 18, 1992

Related U.S. Application Data

[62] Division of Ser. No. 580,455, Sep. 11, 1990, abandoned.

[30] Foreign Application Priority Data

Sep. 11, 1989 [FR] France .................. 89 11823

[51] Int. Cl.$^5$ .................. A61K 9/00
[52] U.S. Cl. .................. 424/400; 210/321.84; 215/261; 215/308; 215/310; 220/203; 220/367; 220/371; 220/373; 239/34; 239/57; 239/58; 422/102; 422/104; 424/424; 609/892.1
[58] Field of Search .................. 424/400, 424; 210/321.84; 215/261, 308, 310; 220/203, 367, 371, 373; 239/34, 57, 58; 422/102, 104; 604/892.1

[56] References Cited

U.S. PATENT DOCUMENTS

| | | | |
|---|---|---|---|
| 3,521,784 | 7/1970 | Gaines et al. | 215/261 |
| 3,557,989 | 1/1971 | Balda | 215/261 |
| 3,749,646 | 7/1973 | Pirt | 435/254 |
| 3,760,804 | 9/1973 | Higuchi | 604/892.1 |
| 3,760,805 | 9/1973 | Higuchi | 604/892.1 |
| 3,916,899 | 11/1975 | Theeuwes et al. | 424/424 |
| 3,946,734 | 3/1976 | Dedrick et al. | 604/892.1 |
| 3,951,293 | 4/1976 | Schulz | 215/261 |
| 3,977,404 | 8/1976 | Theeuwes | 424/427 |
| 4,300,558 | 11/1981 | Eckenhoff et al. | 604/892.1 |
| 4,618,487 | 10/1986 | DuBois et al. | 424/467 |
| 4,769,144 | 9/1988 | Nohren, Jr. | 210/282 |

FOREIGN PATENT DOCUMENTS

| | | |
|---|---|---|
| 0040457 | 11/1981 | European Pat. Off. |
| 262422 | 4/1988 | European Pat. Off. |
| 2182559A | 11/1983 | United Kingdom |

*Primary Examiner*—Thurman K. Page
*Assistant Examiner*—Robert H. Harrison
*Attorney, Agent, or Firm*—Finnegan, Henderson, Farabow, Garrett & Dunner

[57] ABSTRACT

An apparatus is provided for continuous and regular liberation of active constituents into domestic water supplies. The apparatus comprises a receptacle having a body portion which is impermeable to water and to the active constituent. The receptacle is provided with an aperture closed by a membrane which is permeable to water and to the active constituent. An operculum surrounds the membrane to secure the membrane to the receptacle. The active constituent is provided into the receptacle and is released through the membrane in a controlled manner over an extended period of time. Preferably, the membrane has a mean pore diameter greater than 0.05 microns.

5 Claims, 9 Drawing Sheets

METHOD FOR CONTINUOUS LIBERATION OF ACTIVE CONSTITUENTS INTO WATER

This application is a division of application Ser. No. 07/580,455 filed Sep. 11, 1990, abandoned.

BACKGROUND OF THE INVENTION

1. Field of the Invention

The present invention relates to a method and apparatus for continuous and regular liberation of active constituents into water. It relates more particularly to a method and apparatus for continuous liberation of vitamin A into wells and boreholes which provide a source of drinking water.

2. Description of the Related Art

It is estimated that at present several tens of millions of persons have a vitamin A deficiency. This deficiency can result in xerophthalmia, blindness, lowered resistance to infection, and an increase of mortality. The parts of the world which are most affected are Africa, Asia and Latin America. Among these, the zones of the Sahel and the Southern Sahel, namely Benin, Burkina, Faso, Mali and Mauritania, are most gravely affected.

One of the actions being carried out at present by the World Health Organization is distribution of oral doses of 200,000 international units of vitamin A in capsule form twice a year. However, it is difficult to distribute the necessary dose of vitamin A biannually to each inhabitant of the effected areas. Therefore, it would be preferred to provide each inhabitant with vitamin A in a natural manner by means of drinking water. This requires a system for continuous liberation of vitamin A which is easy to implement and allows regular delivery of the vitamin A over prolonged periods. The apparatus used to supply the vitamin A should not need to be changed more than 3 or 4 times per year. This minimizes the number of times a person must visit water points which are often widely dispersed in these desert zones.

There exist numerous patents describing the regular liberation of active constituents, among them vitamins, in the human or animal body. Such patents include, for example, U.S. Pat. Nos. 3,946,734 and 3,977,404, and European Patent Nos. 40,457 and 262,422. These patents are not directed to the problem which the present invention attempts to solve.

There also exist patents which disclose an apparatus for regular liberation of active constituents into the surrounding medium. Such patents include, for example, U.S. Pat. Nos. 4,300,558 and 4,618,487, European Patent No. 40,457 and British Patent No. 2,182,559. These patents disclose an apparatus which establishes an osmotic difference between the interior of an apparatus, which contains the active constituent to be diffused and a mineral salt, and the exterior of the apparatus. The large quantity of salt attracts water from the exterior environment which enters through the wall of the apparatus. This water, along with the dissolved salt and the active constituent, escape through an orifice made in the wall of the apparatus. The exterior wall is generally permeable to water and impermeable to the active constituent.

Such an apparatus is disadvantageous because it requires the manufacture of a delivery system made of a semi-permeable material. It is also disadvantageous because it requires the use of a large quantity of mineral salt which will inevitably be liberated with the active constituent. In the case of the addition of an active constituent, such as vitamin A, to drinking water, it is desired to liberate the minimum amount of salt in order not to modify the taste of the water.

SUMMARY OF THE INVENTION

The present invention overcomes the problems and disadvantages of the prior art by providing a method and apparatus for the continuous and regular liberation of an active constituent into water.

One object of the present invention is to provide a method and apparatus for supplying an active constituent, such as vitamin A, into drinking water without modifying the taste of the water.

It is another object of the present invention to provide a method and apparatus for continuous supplying of an active constituent into water over an extended period of time without any human intervention.

Additional objects and advantages of the invention will be set forth in the description which follows, and in part will be obvious from the description or may be learned by practice of the invention. The objects and advantages of the invention may be realized and obtained by means of the instrumentalities and combinations particularly pointed out in the appended claims.

To achieve the forgoing objects in accordance with the invention as embodied and broadly described herein, there is provided an apparatus for continuous and regular liberation of an active constituent into water. The apparatus comprises a receptacle for receiving and storing the active constituent. The receptacle includes a body portion and an aperture, the body portion being impermeable to water and to the active constituent. The apparatus also includes a membrane that closes the aperture, the membrane being permeable to water and to the active constituent. The apparatus further includes an operculum surrounding the membrane to secure the membrane to the receptacle.

In another aspect of the present invention, there is provided a method for continuous and regular liberation of the active constituent into water. The method includes introducing the active constituent into a receptacle having an aperture and a body portion, the body portion being formed of a material impermeable to water and to the principle. The aperture of the receptacle is closed with a membrane that is permeable to the principle and to water. Finally, the receptacle is immersed in a water supply.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of the specification, illustrate a preferred embodiment of the invention and, together with the general description given above and the detailed description of the preferred embodiment given below, serve to explain the principles of the invention.

DESCRIPTION OF THE PREFERRED EMBODIMENT

Figure 1:
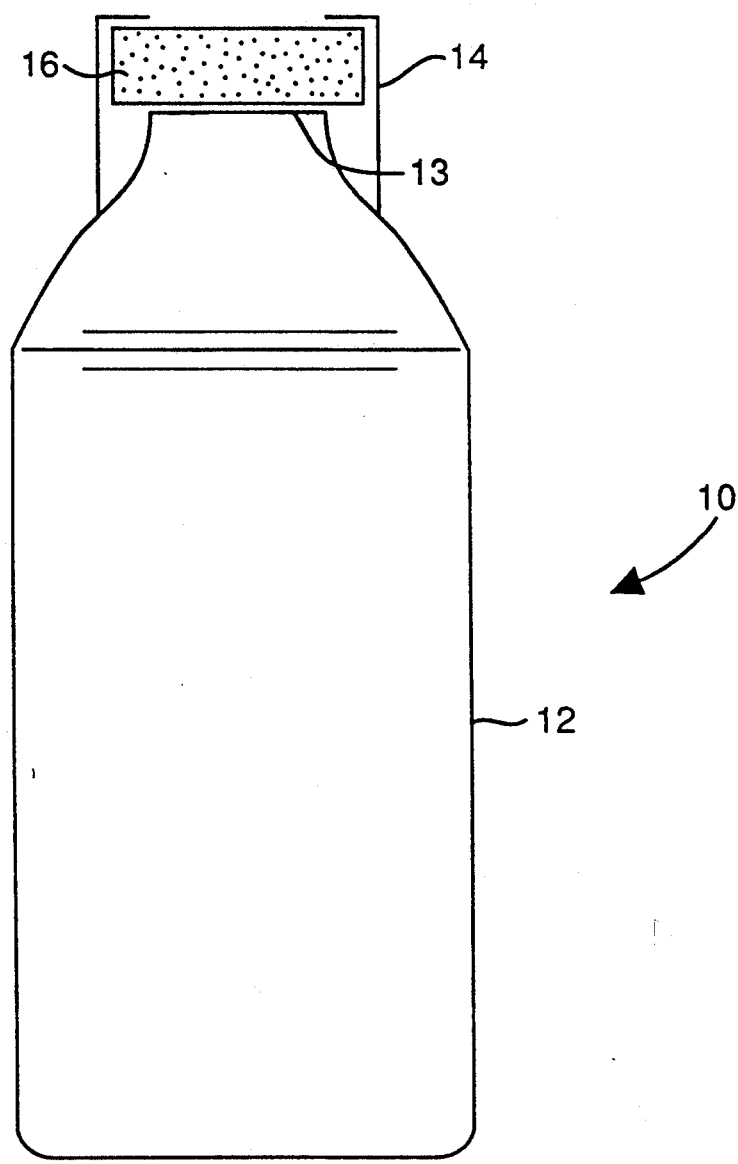
FIG. 1 is a schematic illustration of the apparatus of the present invention.

Reference will now be made in detail to present preferred embodiments of the invention as illustrated in the accompanying drawings. Although the apparatus and method of the present invention are discussed primarily with respect to vitamin A, it should be understood that any number of other compounds or elements can be supplied by means of the present invention. The term "constituent" as used herein means any compound or element that can be dispersed to produce a predetermined beneficial result. The present invention is directed generally to an apparatus that allows continuous and regular liberation of active constituents into domestic water, without the concomitant liberation of mineral salts.

In accordance with the present invention, the present invention includes a receptacle for receiving and storing an active constituent. The receptacle includes a body portion that is impermeable to water and to the active constituent and an aperture. The aperture is closed by a membrane that is permeable to water and to the active constituent. An operculum surrounds the membrane to secure the membrane to the receptacle. As embodied herein, a receptacle indicated generally with the reference character 10 is provided for receiving and storing the active constituent. Receptacle 10 includes a body portion 12 that is impermeable to water and the active constituent. Body portion 12 should be formed of a material that can withstand the environment in which it will be immersed, e.g., a well or borehole. Preferably, body portion 12 is formed of glass or plastic.

Receptacle 10 also includes an aperture 13. As shown schematically in FIG. 1, aperture 13 is closed by a membrane 16 that is permeable to water and to the active constituent. An operculum 14 surrounds membrane 16 to secure the membrane to receptacle 10. Preferably, membrane 16 has a mean pore diameter greater than 0.05 microns. More preferably, membrane 16 has a mean pore diameter between 0.1 and 20.0 microns.

The active constituent can be vitamin A or one of its esters such as palmitate. Vitamin A, being lipophilic, can be introduced into receptacle 10 in a hydrodispersible or hydrosoluble form. The hydrodispersible vitamin A solids sold under the trademarks Cryptovit ® or Microvit ® can be used. Preferably, the vitamin A is introduced into the receptacle in a liquid hydrodispersible form consisting of an oil-in-water emulsion. The use of a hydrodispersible liquid form which is available commercially under the trademark Hydrovit ® (which contains 200,000 IU of vitamin A) is preferred.

The membrane 16 closing the aperture 13 is chosen from materials which are permeable to water and to the vitamin A emulsion. Materials which can be used for forming the membrane include inorganic polymers such as acrylic polymers, vinyl polychlorides, cellulose esters, polysulphones, polycarbonates, vinylidene polyfluorides, and polytetrafluoroethylenes. Also, inorganic polymers such as ceramics may be utilized to close the operculum.

In accordance with the present invention, there is provided a method for continuous and regular liberation of an active constituent into water. The method includes introducing the constituent into a receptacle having an aperture and a body portion. The body portion is formed of a material impermeable to water and to the constituent. The aperture is closed with a membrane that is permeable to water and to the constituent. Finally, the receptacle is immersed in a water supply.

The apparatus of the present invention is immersed in places containing the water to be treated. In particular, the apparatus is intended for immersion in wells and boreholes to liberate an appropriate quantity of vitamin A in a continuous manner at a dose which is sufficient to ensure the indispensable minimum for human and animal consumption without, however, reaching toxic doses which are estimated to be about 600,000 IU per 24 hours per inhabitant.

The surface area and the mean pore diameter of the membrane can be determined by those skilled in the art as a function of the desired flow rate of the vitamin A. A flow of Hydrovit ® between 5 and 50 mg per square centimeter of membrane per hour would appear to be sufficient. In order to allow these flows, membranes having surface areas of 30 to 100 $cm^2$ (which corresponds to opercula of 3 to 6 cm diameter) and having pore diameters from 1.5 $\mu$ to 0.5 $\mu$ may be used.

According to the present invention, a vitamin A emulsion sold under the trademark Hydrovit ® may be used in a well with a flow rate of 600 liters of water per hour. It may be desirable to liberate 250 micrograms of vitamin A per liter for a period of at least 3 months. This flow rate allows absorption by each human being of a daily dose of vitamin A of 500 micrograms, if a typical individual absorbs about 2 liters of water per day. In this case, about 5 kg of Hydrovit ® would be introduced into a flask provided with a microfiltration membrane the surface area and pore size characteristics of which are suitable for the desired flow rate of vitamin A.

The present invention will be more completely described with the aid of the following examples which must not be considered as limiting the invention.

EXAMPLE 1

Hydrovit ® (250 ml) containing 200,000 IU is introduce 250 ml glass receptacle having an orifice with a surface area of 1 $cm^2$. The orifice is then closed with a microporous membrane, the mean pore diameter of which is equal to 1.5 $\mu$m (reference: Techsep Iris ® 56-25). The membrane is inserted between two Teflon ® joints and is fixed to the receptacle with a screw cap. The Teflon ® joints act as a seal to prevent leakage around the membrane. The assembly is then immersed in a container containing distilled water (4 liters) which is protected from light. The container is equipped with a slow-moving magnetic stirring system (100 rev/min) which ensures the solution is homogeneous. It is necessary to agitate the solution to overcome an increase in vitamin concentration near the membrane which would affect further diffusion of the vitamin.

Samples are taken from the container every two days. The distilled water is changed at each sampling in order to maintain "sink" conditions. By "sink" conditions it is understood dilution conditions such that there is no limiting-layer phenomenon in the neighborhood of the membrane.

Figure 2:
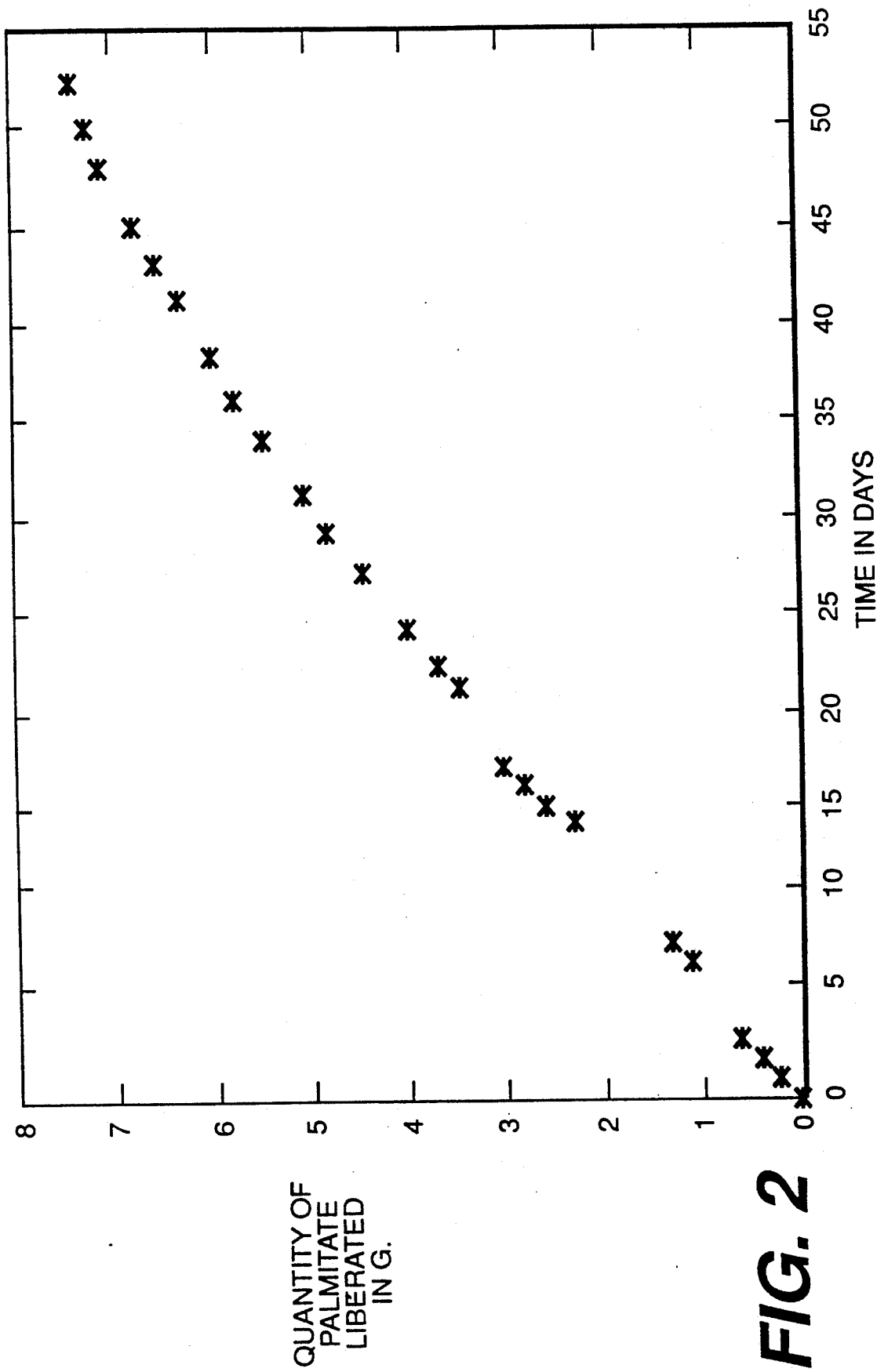
FIG. 2 is a graph illustrating the amount of active constituents liberated over time in a first example of the present invention.
Figure 3:
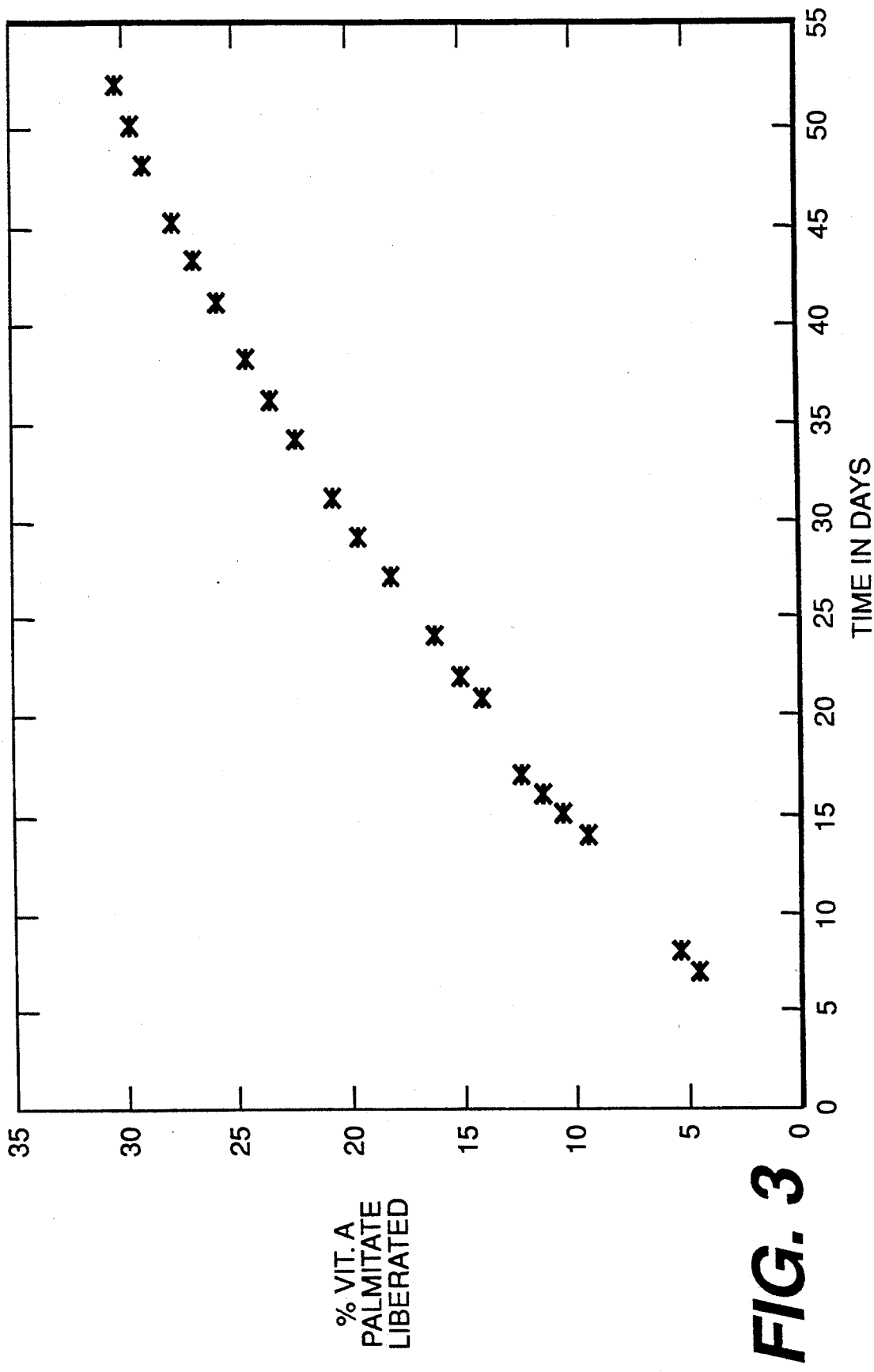
FIG. 3 is a graph illustrating the percentage of active constituent liberated over time in the first example of the present invention.

The vitamin A concentration in the container is determined by UV spectrophotometric measurement at a wavelength of 316 nm. A calibration curve established beforehand using standard solutions of concentrations between 1 and 15 mg/l (vitamin A palmitate) allows the concentration of the solution to be obtained. The curve corresponding to the elution kinetic is shown in FIG. 2, which illustrates quantity of vitamin A palmitate liberated as a function of time. The curve of the percentage of vitamin A palmitate liberated as a function of time for the same elution kinetic is shown in FIG. 3.

In this example, controlled liberation of vitamin A over periods of 3 months (in the example 30% was eluted in 50 days) and daily flow rates corresponding to the objective (about 300 mg/d vitamin A palmitate) were obtained using a 40 cm² membrane.

EXAMPLE 2

Hydrovit (250 ml) containing 200,000 IU is introduced into a 250 ml glass receptacle having an orifice with a surface area of 1.8 cm². The orifice is then closed with a microporous membrane, the mean pore diameter of which is equal to 0.1 μm (reference: Techsep Iris ® 65-02). The membrane is inserted between two Teflon ® joints and fixed to the receptacle using a screw cap. The assembly is then immersed in a container containing distilled water (4 liters) which is protected from light. The container is equipped with a slow-moving magnetic stirring system (100 rev/min) which ensures the solution is homogeneous.

Figure 4:
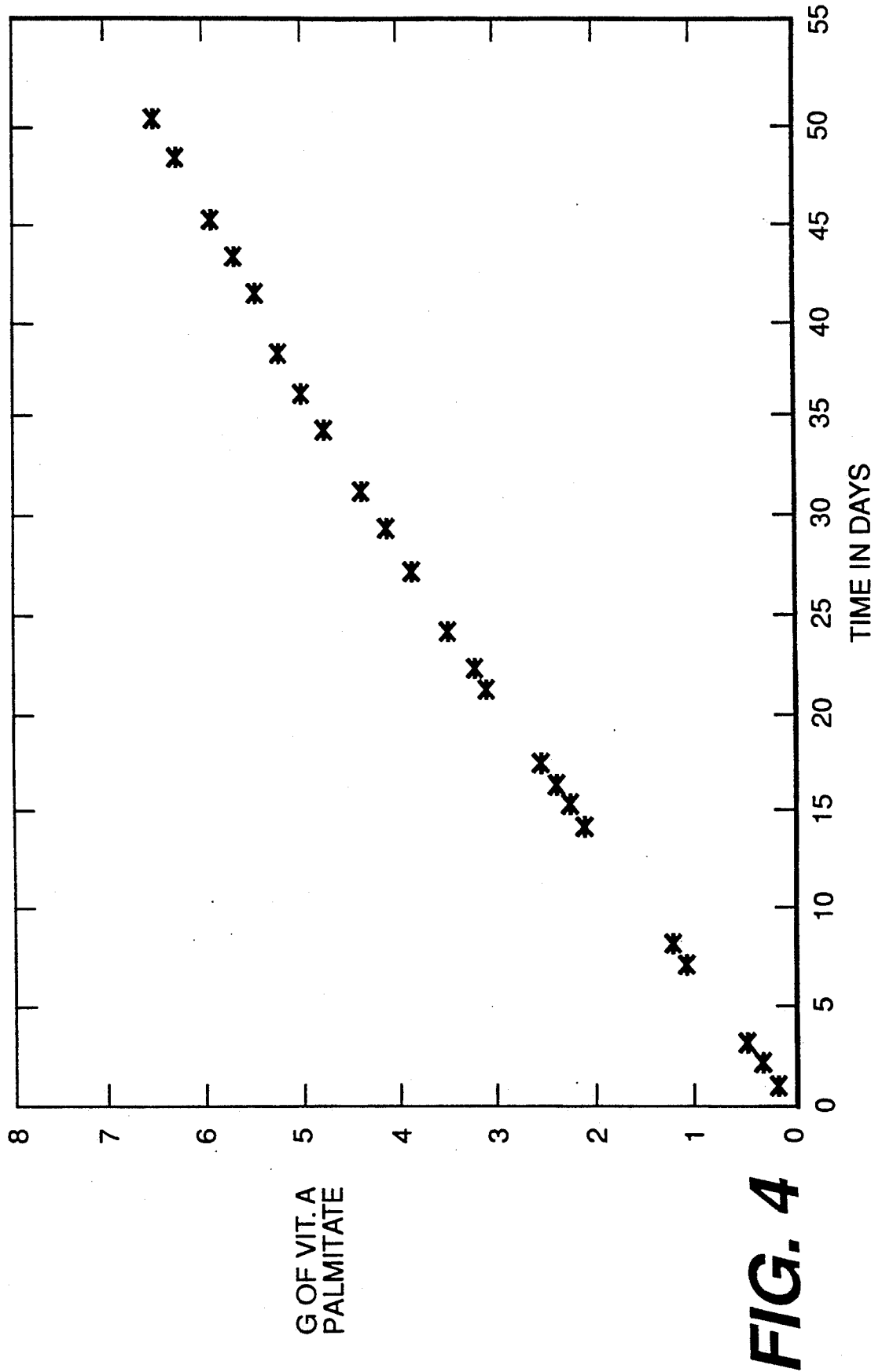
FIG. 4 is a graph illustrating the amount of active constituent liberated over time in a second example of the present invention.
Figure 5:
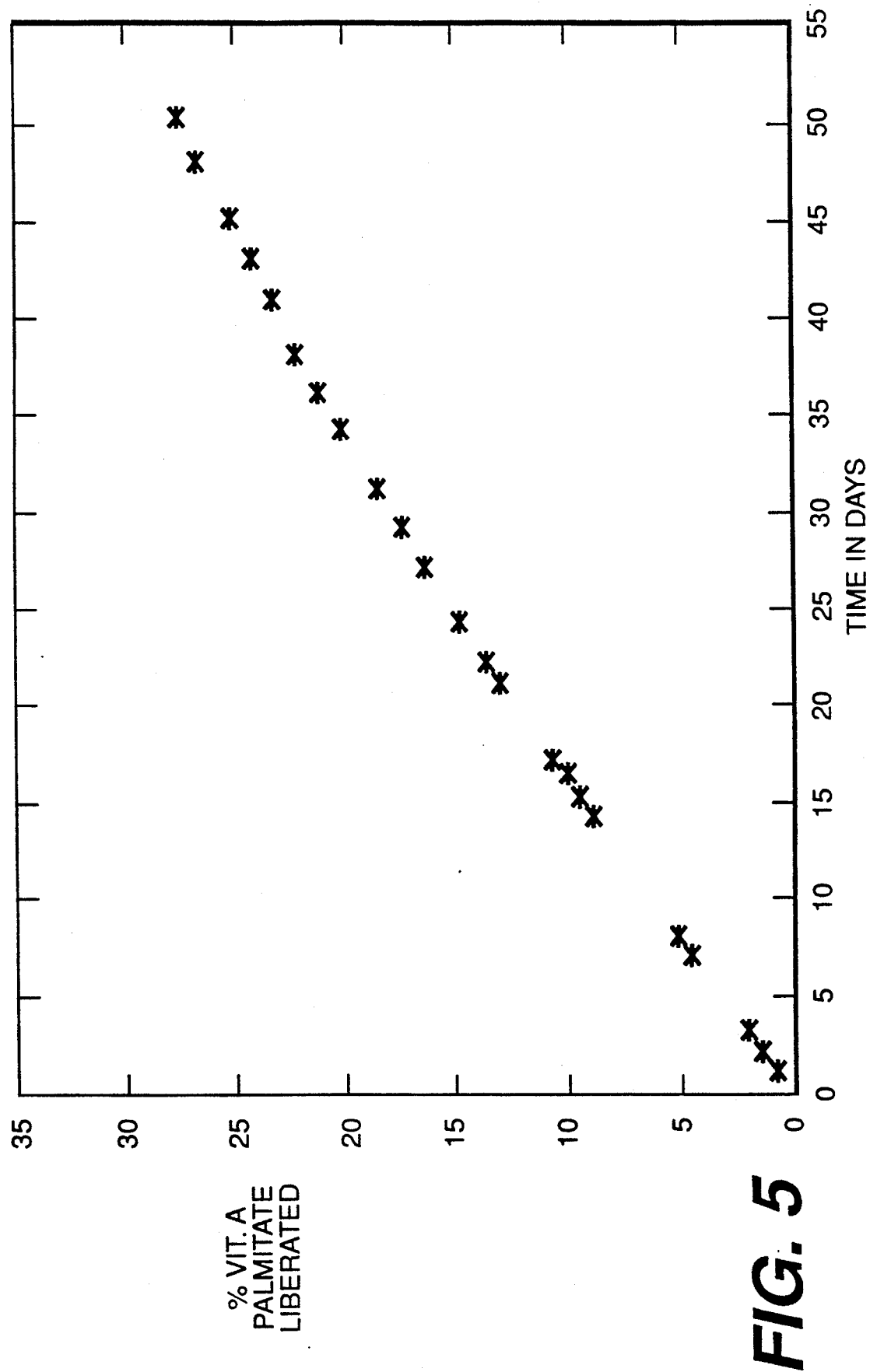
FIG. 5 is a graph illustrating the percentage of active constituent liberated over time in the second example of the present invention.

Samples are taken every two days. The distilled water is changed at each sampling in order to maintain "sink" conditions. The vitamin A concentration is determined by UV spectrophotometric measurement at a wavelength of 316 nm. A calibration curve established beforehand using standard solutions of concentrations between 1 and 15 mg/l (vitamin A palmitate) allows the concentration of the solution to be obtained. The curve corresponding to the elution kinetics, that is, the quantity of vitamin A palmitate liberated as a function of time is shown in FIG. 4. The curve of the percentage of vitamin A liberated as a function of time for the same elution kinetics is shown in FIG. 5.

In this example, controlled liberation of vitamin A over a period of 3 months (in the example 30% was eluted in 50 days) and daily flow rates corresponding to the objective (about 300 mg/d vitamin A palmitate) can be obtained using a 75 cm² membrane.

EXAMPLE 3

The assembly of example three is the same as the assembly for example one, with the exception of the membrane. The membrane of example three measures 1 cm² and has a mean pore diameter of 0.22 μm. The membrane is formed of a cellulose ester and is identified with the trademark MF-MILLIPORE/GS.

Figure 6:
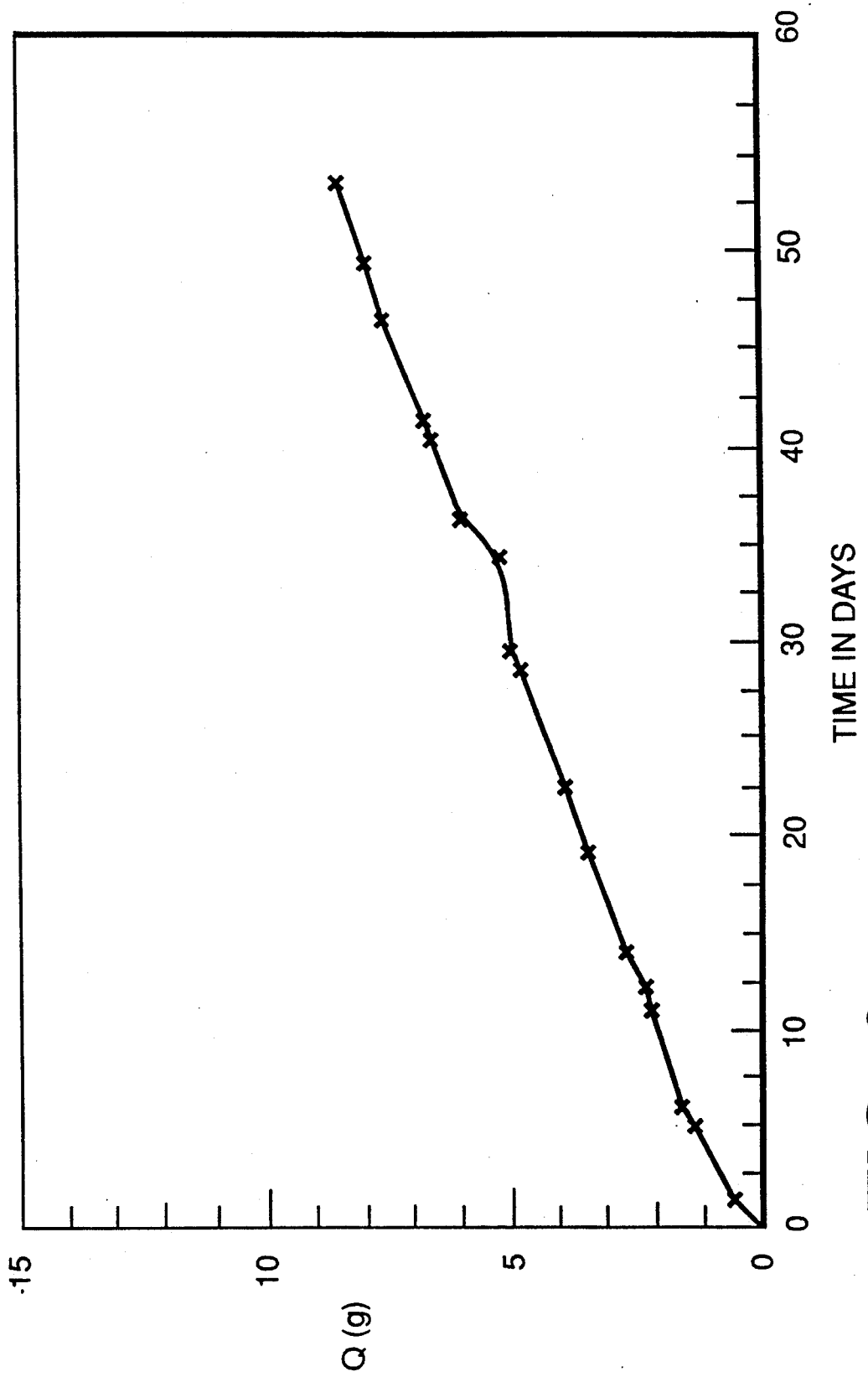
FIG. 6 is a graph illustrating the amount of active constituent liberated over time in a third example of the present invention.
Figure 7:
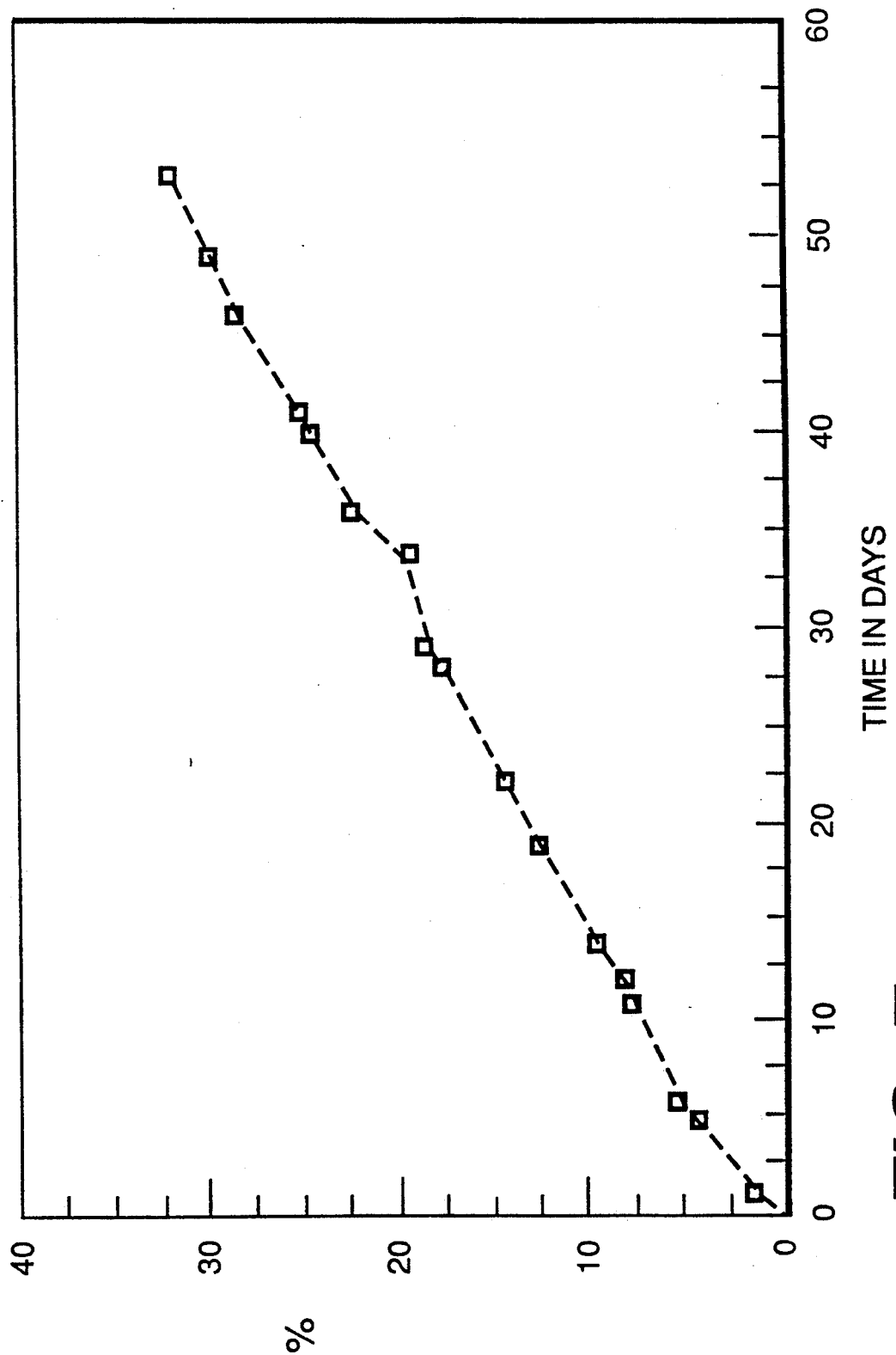
FIG. 7 is a graph illustrating the percentage of active constituent liberated over time in the third example of the present invention.

The quantity of active constituent liberated over a period of time is indicated in FIG. 6. The percentage of active constituent liberated over a period of time is indicated in FIG. 7. FIGS. 6 and 7 are based on the same sampling and measurement techniques described in example one. Based on the results of example three, it is expected that an objective of liberating 7.2 grams per day could be achieved by using a membrane with a surface area of 45 cm².

EXAMPLE 4

The assembly of example four is the same as the assembly used in example three, with the exception of the membrane. The membrane of example 4 also has a mean pore diameter of 0.22 μm, but is a polyvinylidene fluoride membrane treated to become a hydrophile. (reference: DURAPORE/GV ®).

Figure 8:
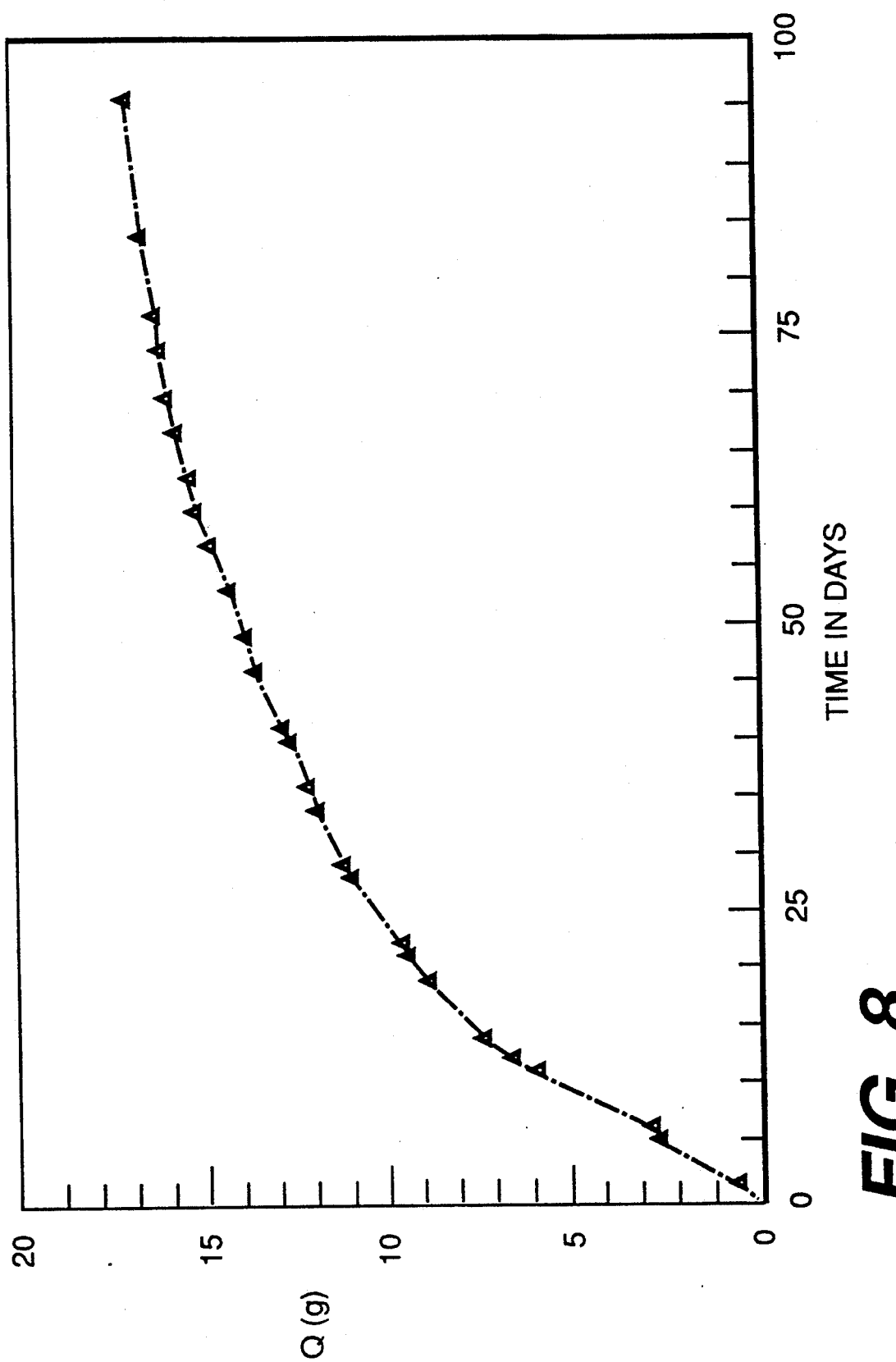
FIG. 8 is a graph illustrating the amount of active constituent liberated over time in a fourth example of the present invention.
Figure 9:
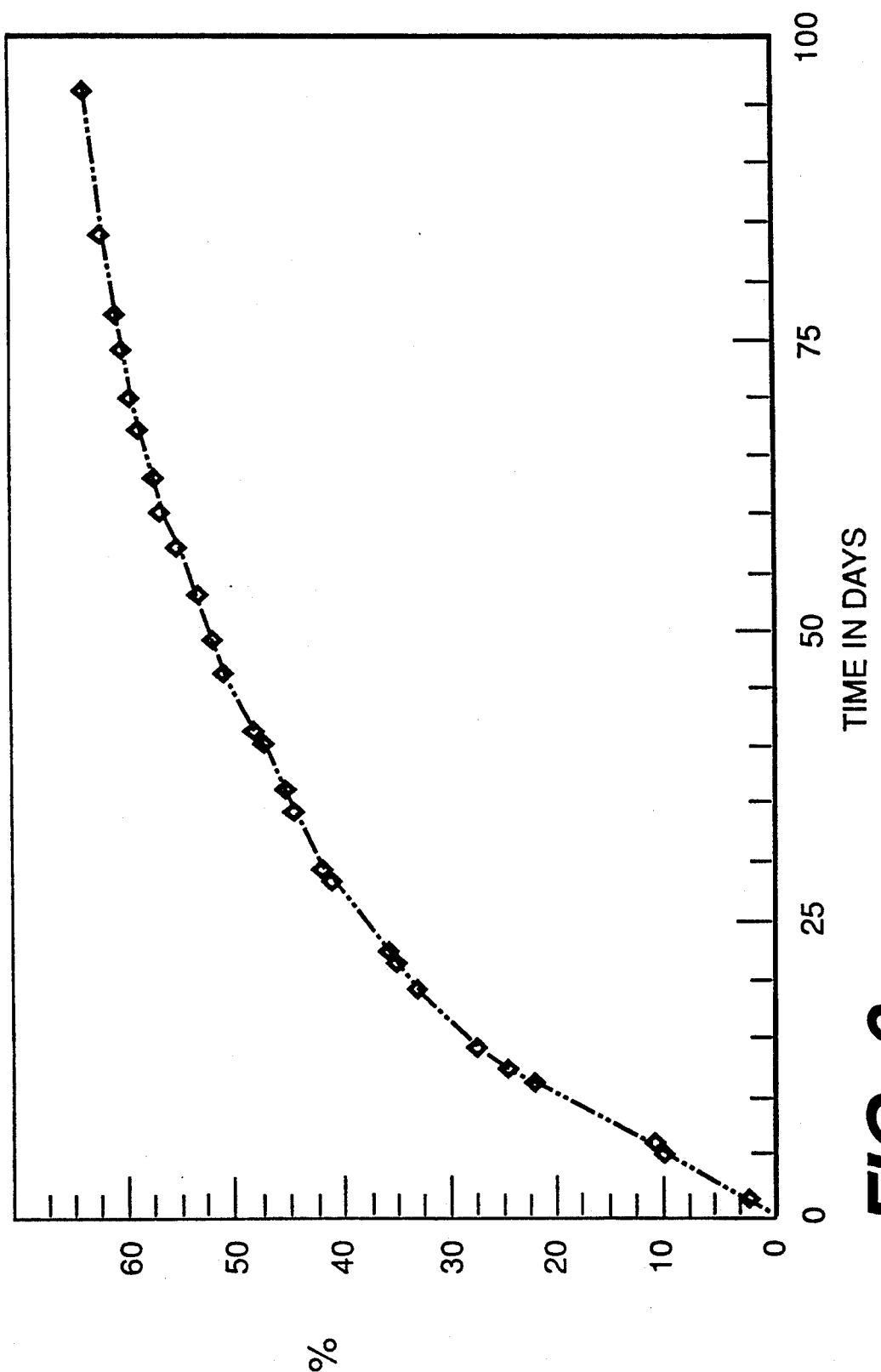
FIG. 9 is a graph illustrating the percentage of active constituent liberated over time in the fourth example of the present invention.

The quantity of active constituent liberated over a period of time is indicated in FIG. 8. The percentage of active constituent liberated over a period of time is indicated in FIG. 9. FIGS. 8 and 9 are based on the same sampling and measurement techniques described in example one. Based on the results of example four, it is expected that the objective of liberating 7.2 grams per day could be achieved by using a membrane with a surface area of 20 cm².

It will be apparent to those skilled in the art that various modifications and variations can be made to the apparatus and method of the present invention without departing from the scope or spirit of the present invention. Thus, it is intended that the present invention covers the modifications and variations of the invention which come within the scope of the appended claims or their equivalents.

What is claimed is:

1. A method for continuous and regular liberation of a vitamin into a well or borehole, the method comprising the steps of:
   introducing a vitamin into a receptacle having an aperture and a body portion, the body portion being formed of a material impermeable to water and to the vitamin;
   closing the aperture with a membrane that is permeable to the vitamin and to water; and
   immersing the receptacle in a well or borehole to permit diffusion of the vitamin through the membrane into the well or borehole over at least a month.

2. The method of claim 1, wherein the vitamin is vitamin A.

3. The method of claim 1, wherein the receptacle is immersed in the well or borehole in a fixed position.

4. The method of claim 1, wherein the vitamin is diffused into the water for a period of at least 3 months.

5. The method of claim 1, wherein the vitamin is diffused at a rate of between 5 and 50 mg per square centimeter of membrane per hour.

* * * * *